United States Patent [19]

Miura

[11] Patent Number: 5,062,794
[45] Date of Patent: Nov. 5, 1991

[54] ORTHODONTIC APPLIANCE WITH SHOULDER SUPPORT FOR LIGATURE

[75] Inventor: Fujio Miura, Tokyo, Japan

[73] Assignee: GAC International, Inc., Central Islip, N.Y.

[21] Appl. No.: 503,293

[22] Filed: Apr. 2, 1990

[30] Foreign Application Priority Data

Jun. 20, 1989 [JP] Japan .................................. 1-155895

[51] Int. Cl.⁵ .............................................. A61C 3/00
[52] U.S. Cl. ............................................ 433/10; 433/8
[58] Field of Search ......................... 433/8, 9, 10, 11

[56] References Cited

U.S. PATENT DOCUMENTS

| | | | |
|---|---|---|---|
| D. 289,329 | 4/1987 | Evans | D24/16 |
| D. 290,040 | 5/1987 | Kelly | D24/16 |
| D. 291,919 | 9/1987 | Reynolds | D24/10 |
| D. 304,077 | 10/1989 | Pospisil | D24/16 |
| 3,303,565 | 2/1967 | Newman | 32/14 |
| 3,391,461 | 7/1968 | Johnson | 32/14 |
| 4,260,375 | 4/1981 | Wallshein | 433/11 |
| 4,322,206 | 3/1982 | Reynolds | 433/9 |
| 4,487,581 | 12/1984 | Adler | 433/16 |
| 4,559,012 | 12/1985 | Pletcher | 433/10 |
| 4,799,882 | 1/1989 | Kesling | 433/8 |
| 4,838,786 | 6/1989 | Reher et al. | 433/9 |
| 4,927,360 | 5/1990 | Pospisil | 433/8 |

Primary Examiner—John J. Wilson
Assistant Examiner—Cindy A. Cherichetti
Attorney, Agent, or Firm—Kenyon & Kenyon

[57] ABSTRACT

An orthodontic appliance has a bracket portion with an archwire slot formed therein. The archwire slot extends in the mesial-distal direction of the appliance and is dimensioned to receive an archwire. The orthodontic appliance has at least one pair of tie-wings. Each tie-wing projects outwardly from the bracket portion on an opposite side of the archwire slot with respect to the other tie-wing. One pair of opposing shoulders are located on the mesial end of the bracket portion, and another pair of opposing shoulders are located on the distal end of the bracket portion. Each shoulder is located on an opposite side of the archwire slot relative to the other shoulder of the pair. Each shoulder is adapted to support a ligature thereon, and is dimensioned and located with respect to the archwire slot, so that the ligature is spaced above an archwire received therein. The orthodontic appliance is therefore permitted to move relative to the archwire during orthodontic treatment.

17 Claims, 6 Drawing Sheets

ORTHODONTIC APPLIANCE WITH SHOULDER SUPPORT FOR LIGATURE

FIELD OF THE INVENTION

The present invention relates to orthodontic appliances and, in particular, to orthodontic appliances having bracket portions and means for ligating orthodontic archwires thereto.

BACKGROUND INFORMATION

An orthodontic appliance typically comprises a bracket portion having an archwire slot formed therein, which is dimensioned to receive an archwire. The archwire slot extends in the mesial-distal direction of the appliance. Tie-wings project outwardly from either side of the archwire slot. A base member is typically fixed to the underside of the bracket portion. The orthodontic appliance is mounted to a tooth by applying adhesive to the base member and mounting the base member to the face of the tooth. With other types of orthodontic appliances, the bracket portion is welded to a thin metal strip or band. The band is in turn wrapped around the tooth and fixed relative thereto by tooth bonding cement.

The orthodontic archwire is then fitted into the archwire slot and ligated to the orthodontic appliance. Typically, a stainless steel ligature wire or elastic member is fitted under the archwire and wrapped around the tie-wings to ligate the archwire to the appliance. The resultant bending and tension within the wire imparts forces to the appliance which are in turn imparted to the tooth. The archwire must be securely ligated to the orthodontic appliance to move the tooth as desired. The force of the archwire can then be accurately imparted to the appliance and, therefore, accurately imparted to the tooth.

During orthodontic treatment, it is necessary for the orthodontic appliance to be able to move relative to the archwire. The forces imparted by the archwire are intended to move the tooth. Therefore, the appliance, which is firmly attached to the tooth, must be permitted to move with the tooth relative to the archwire. One problem with known orthodontic appliances, however, is that the ligature becomes securely engaged with both the archwire and the appliance. As a result, the appliance cannot move freely with the tooth relative to the archwire during treatment. And, accordingly, the tooth cannot move freely in response to the force of the archwire. The outcome of the orthodontic treatment is unpredictable.

One approach to solving this problem, has been to ligate the archwire to the orthodontic appliance with a stainless steel ligature wire, so that a space is maintained between the ligature wire and the orthodontic archwire. The archwire is then usually permitted to slide relative to the orthodontic appliance to permit tooth movement. One problem with this approach, however, is that it is difficult for the clinician to accurately twist the ligature wire so that an appropriate space is maintained between the ligature wire and the orthodontic archwire. This has also proven to be a relatively time-consuming and, therefore, expensive procedure.

With elastic ligatures, on the other hand, it has not been possible to ligate an archwire in such a way that permits the elastic and orthodontic appliance to move relative to the archwire. It has been difficult, therefore, to achieve free tooth movement with elastic ligatures.

The problem of permitting orthodontic appliances to move relative to an orthodontic archwire is enhanced with ceramic orthodontic appliances. There is typically a greater degree of friction between ceramic surfaces and an orthodontic archwire than between metal surfaces and an orthodontic archwire. This problem is further enhanced with orthodontic archwires that are coated with a polymeric material. The polymeric material tends to further increase the level of friction between the archwire and the ceramic appliances.

It is an object of the present invention, therefore, to provide orthodontic appliances that overcome the problems and disadvantages associated with ligating archwires to known orthodontic appliances.

SUMMARY OF THE INVENTION

The present invention is directed to an orthodontic appliance including a bracket portion and an archwire slot defined therein. The archwire slot extends substantially in the mesial-distal direction of the appliance and is adapted to receive an archwire therein.

The bracket portion includes four shoulders on the free end thereof. Two shoulders are located on opposite sides of the archwire slot with respect to each other on the mesial end of the appliance. The other two shoulders are located on opposite sides of the archwire slot with respect to each other on the distal end of the appliance. Each shoulder is adapted to support a ligature thereon so that a space is maintained between the ligature and an archwire received within the archwire slot. The orthodontic appliance is therefore permitted to move relative to the archwire during orthodontic treatment.

An orthodontic appliance of the present invention further comprises at least one pair of tie-wings. Each tie-wing projects outwardly from the bracket portion on an opposite side of the archwire slot with respect to the other tie-wing. The pair of tie-wings are located between the two shoulders on the mesial end of the appliance and the two shoulders on the distal end of the appliance. The tie-wings are each adapted so that ligature can be wrapped underneath each tie-wing and over the shoulders to ligate an archwire to the appliance.

In one orthodontic appliance of the present invention, each shoulder is defined by a substantially curved surface extending upwardly on the bracket portion and terminating on an edge of the archwire slot. In another orthodontic appliance of the present invention, each shoulder is defined substantially by a surface extending outwardly from the adjacent tie-wing and located substantially in the same plane as the top surface of the tie-wing.

Another orthodontic appliance of the present invention comprises two pairs of tie-wings spaced apart from each other. One pair of tie-wings is located adjacent to the two shoulders located on the mesial end of the appliance. The other pair of tie-wings is located adjacent to the two shoulders located on the distal end of the appliance. One orthodontic appliance of the present invention further comprises two shoulders located on opposite sides of the archwire slot with respect to each other and extending between the two pairs of tie-wings. Each shoulder is adapted to support a ligature thereon so that a space is maintained between the ligature and an archwire received within the archwire slot. The orthodontic appliance is therefore permitted to move relative to the archwire during orthodontic treatment. Preferably, each shoulder is defined by a substantially curved surface extending upwardly on the bracket portion and terminating on an edge of the archwire slot.

In another orthodontic appliance of the present invention, the two shoulders located on the mesial end of the appliance are defined by a first member projecting outwardly from the bracket portion and having one end of the archwire slot formed therethrough. The two shoulders located on the distal end of the appliance are defined by a second member projecting outwardly from the bracket portion and having the other end of the archwire slot formed therethrough. Each shoulder is defined by a substantially curved surface of the first or second member, respectively, extending downwardly from the adjacent edge of the archwire slot in substantially the direction of the base member.

The present invention is also directed to another orthodontic appliance comprising a bracket portion defining an archwire slot extending therethrough. The archwire slot is adapted to receive an archwire therein. The orthodontic appliance further comprises means for supporting a ligature on the bracket portion for maintaining a space between the ligature and an archwire received within the archwire slot. The orthodontic appliance is therefore permitted to move relative to the archwire during orthodontic treatment.

In one orthodontic appliance of the present invention, the means for supporting includes a first pair of shoulders, each shoulder being located on an opposite side of the archwire slot relative to the other on the free end of the bracket portion. Each shoulder is adapted to support a ligature thereon so that when an archwire is received within the archwire slot, the ligature is spaced above the archwire. The orthodontic appliance further comprises a first pair of tie-wings. Each tie-wing is located on an opposite side of the archwire slot relative to the other and projects outwardly therefrom. Each tie-wing is located adjacent to a respective shoulder.

The means for supporting preferably further includes a second pair of shoulders located on an opposite side of the appliance with respect to the first pair of shoulders on the free end of the bracket portion. Each of the second shoulders is located on an opposite side of the archwire slot relative to the other. The pair of tie-wings is located between the first and second pairs of shoulders. One orthodontic appliance of the present invention further includes a second pair of tie-wings. Each second tie-wing is located on an opposite side of the archwire slot relative to the other and projects outwardly therefrom. The second pair of tie-wings is spaced apart from the first pair of tie-wings. The first and second pairs of tie-wings are therefore each located adjacent to the first and second pairs of shoulders, respectively.

One advantage of the orthodontic appliance of the present invention, is that each shoulder is dimensioned and located relative to the archwire slot to support a ligature so that it is spaced above an archwire received therein. The ligature therefore does not engage the archwire as with other known orthodontic appliances and, accordingly, does not prevent the orthodontic appliance from moving with the tooth relative to the archwire during orthodontic treatment. The orthodontic appliance of the present invention permits both stainless steel ligature wires or elastic ligatures to be used to securely ligate an archwire thereto while permitting the archwire to move relative thereto. The problems encountered with known orthodontic appliances that do not permit free tooth movement are therefore overcome by the orthodontic appliance of the present invention.

Other advantages of the orthodontic appliance of the present invention will become apparent in view of the following detailed description and drawings taken in connection therewith.

DETAILED DESCRIPTION

Figure 1:
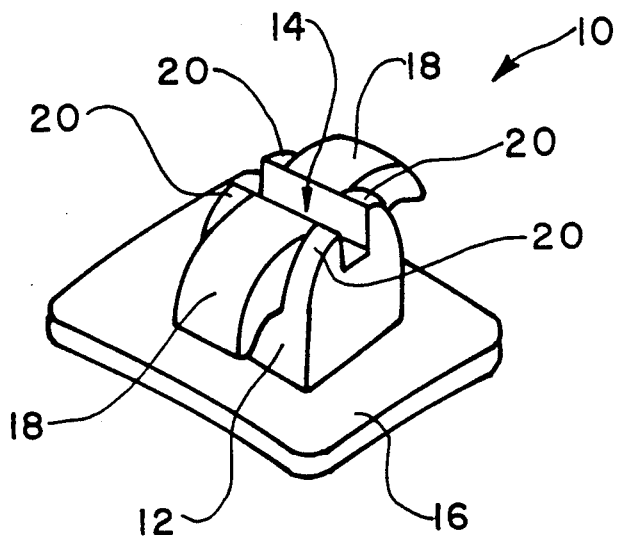
FIG. 1 is a top perspective view of an orthodontic appliance embodying the present invention.
Figure 2:
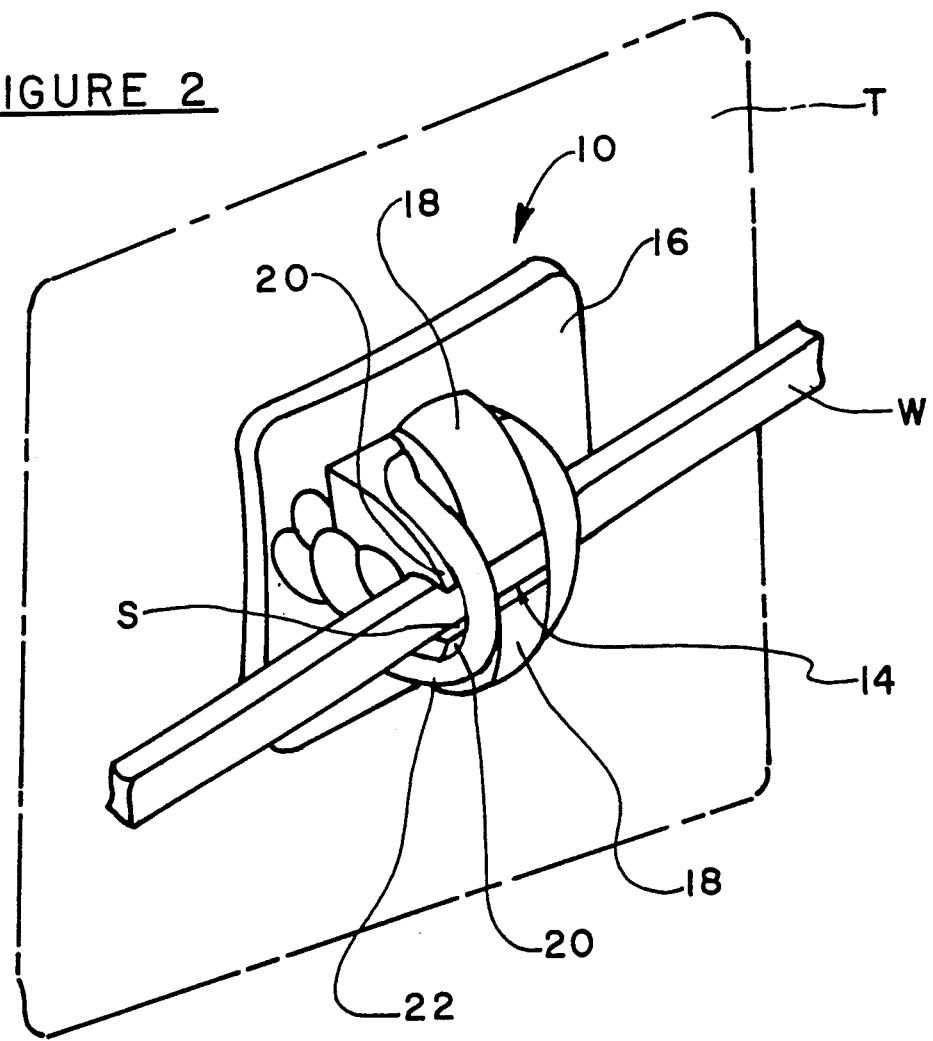
FIG. 2 is another perspective view of the orthodontic appliance of FIG. 1, shown mounted to a tooth with an archwire ligated by a ligature wire thereto.
Figure 3:
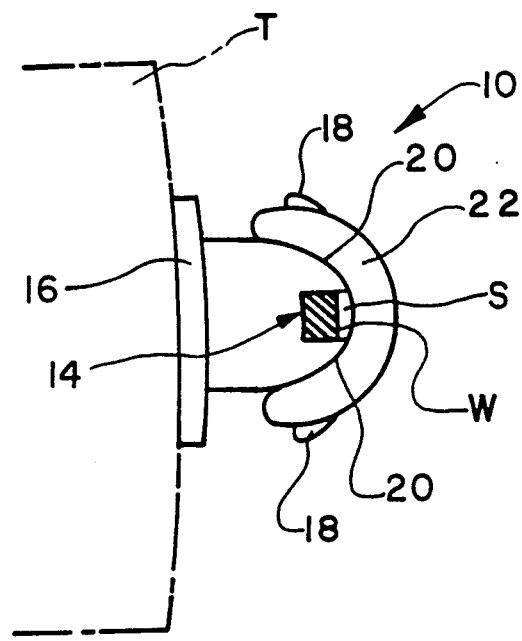
FIG. 3 is a side plan view of the orthodontic appliance of FIG. 2, illustrating the archwire in cross-section.
Figure 4:
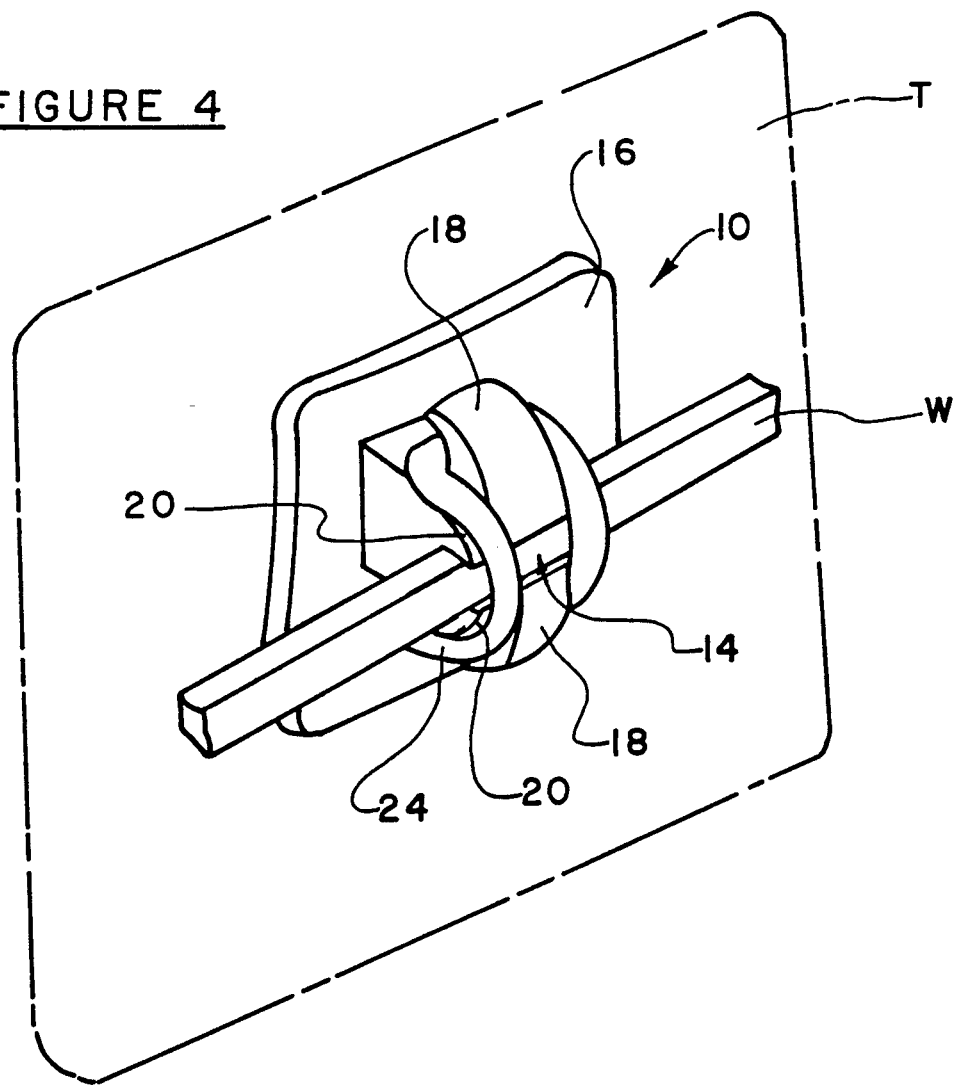
FIG. 4 is another perspective view of the orthodontic appliance of FIG. 1, shown mounted to a tooth with an archwire ligated thereto by an elastic ligature.

In FIG. 1, an orthodontic appliance embodying the present invention is indicated generally by the reference numeral 10. The orthodontic appliance 10 includes a bracket portion 12, having an archwire slot 14 formed therein. The archwire slot 14 is dimensioned to receive an archwire W, as shown in FIGS. 2 through 4. A base member 16 is fixed to the bottom of the bracket portion 12, and is provided to mount the orthodontic appliance 10 to a tooth with a suitable adhesive.

The orthodontic appliance 10 further comprises a pair of tie-wings 18, projecting outwardly from the bracket portion 12 on either side of the archwire slot 14. Four shoulders 20 extend upwardly on the bracket portion 12 on the free end thereof, on either side of the tie-wings 18. There are two opposing mesial shoulders 20 and two opposing distal shoulders 20. For purposes of illustration, the distal shoulders 20 are to the right in the drawings, and the mesial shoulders 20 are to the left in the drawings. Each shoulder 20 is provided to support a ligature, such as a stainless steel ligature wire or an elastic ligature, to secure an archwire W to the orthodontic appliance 10. As shown in FIG. 1, each shoulder 20 has a curved outer surface, which is substantially defined by a radius of curvature, and extends between the top edge of the archwire slot 14 and the bracket portion 12.

In FIG. 2, the orthodontic appliance 10 is shown mounted to a tooth T. An archwire W is fitted within the archwire slot 14, and is ligated to the orthodontic appliance 10 by a stainless steel ligature wire 22. As shown in FIG. 2, the archwire W is seated against the bottom surface of the archwire slot 14. The stainless steel ligature wire 22 is wrapped over the distal shoulders 20, underneath the two tie-wings 18 and, in turn, over the mesial shoulders 20. The two ends of the ligature wire 22 are then wrapped underneath the archwire on the mesial side of the appliance 10, and twisted together, as shown in FIG. 2.

As shown in FIG. 3, the shoulders 20 are dimensioned so that when the archwire W is seated against the bottom surface of the archwire slot 14, the top edge of each shoulder extends above the top surface of the archwire W. A space S is thus maintained between the top of the archwire W and the ligature wire 22. As a result, because the ligature wire 22 is not pressed against the archwire W, but is maintained above the archwire by a space S, the orthodontic appliance 10 is permitted to move with the tooth relative to the archwire W. The tooth T is thus permitted to move freely under the forces of the archwire W. Accordingly, the problems of known orthodontic appliances that cannot move freely relative to the archwire are overcome with the orthodontic appliance 10.

In FIG. 4, the orthodontic appliance 10 is shown mounted to a tooth T with an archwire W ligated to the bracket portion by an elastic ligature 24. The elastic ligature 24 is fitted over the distal shoulders 20, under the tie-wings 18, and over the mesial shoulders 20, to securely ligate the archwire W to the orthodontic appliance 10. Because the elastic ligature 24 is supported by the four shoulders 20, it is spaced above the top of the archwire W by a space S. Therefore, when the tooth T moves during treatment, the orthodontic appliance 10 is permitted to move with the tooth and thus slide relative to the archwire W.

Figure 5:
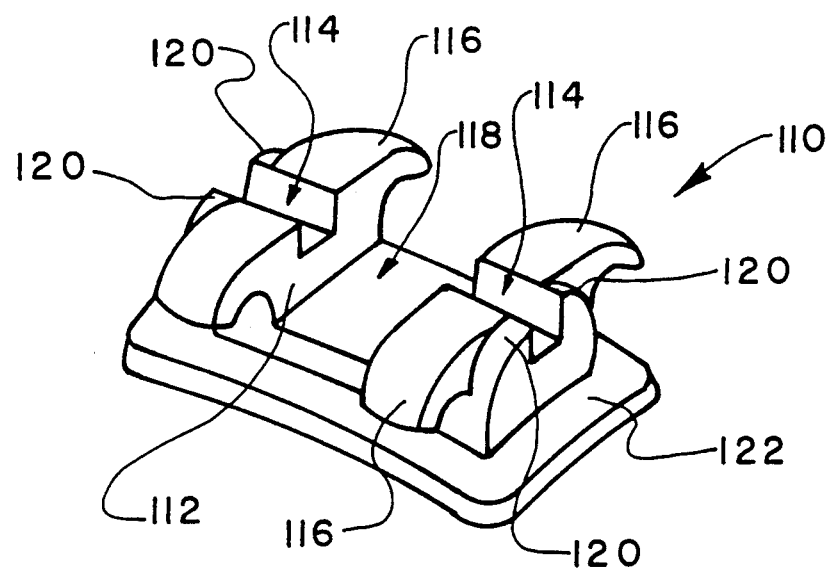
FIG. 5 is a top perspective view of another orthodontic appliance embodying the present invention.

In FIG. 5, another orthodontic appliance embodying the present invention is indicated generally by the reference numeral 110. The orthodontic appliance 110 includes a bracket portion 112, and an archwire slot 114 extending through the bracket portion 112 in the mesial-distal direction thereof. The orthodontic appliance 110 is a twin tie-wing appliance and, therefore, includes two pairs of tie-wings 116. The tie-wings 116 project outwardly from either side of the archwire slot 114. A channel 118 extends through the bracket portion 112 in a direction substantially perpendicular to the archwire slot 114, between the two pairs of tie-wings 116.

The orthodontic appliance 110 further comprises four shoulders 120 extending upwardly on the bracket portion 112 on the free end thereof, on either side of the archwire slot 114. Two opposing shoulders 120 are located on the mesial end of the orthodontic appliance 110, and the other two opposing shoulders 120 are located on its distal end. Each of the shoulders 120 includes a rounded exterior surface which extends upwardly on the bracket portion 112 and terminates on the top edge of the archwire slot 114. Each shoulder 120 is defined substantially by a radius of curvature. The orthodontic appliance 110 further comprises a base member 122, fixed to the underside of the bracket portion 112, for mounting the appliance to a tooth.

Figure 6:
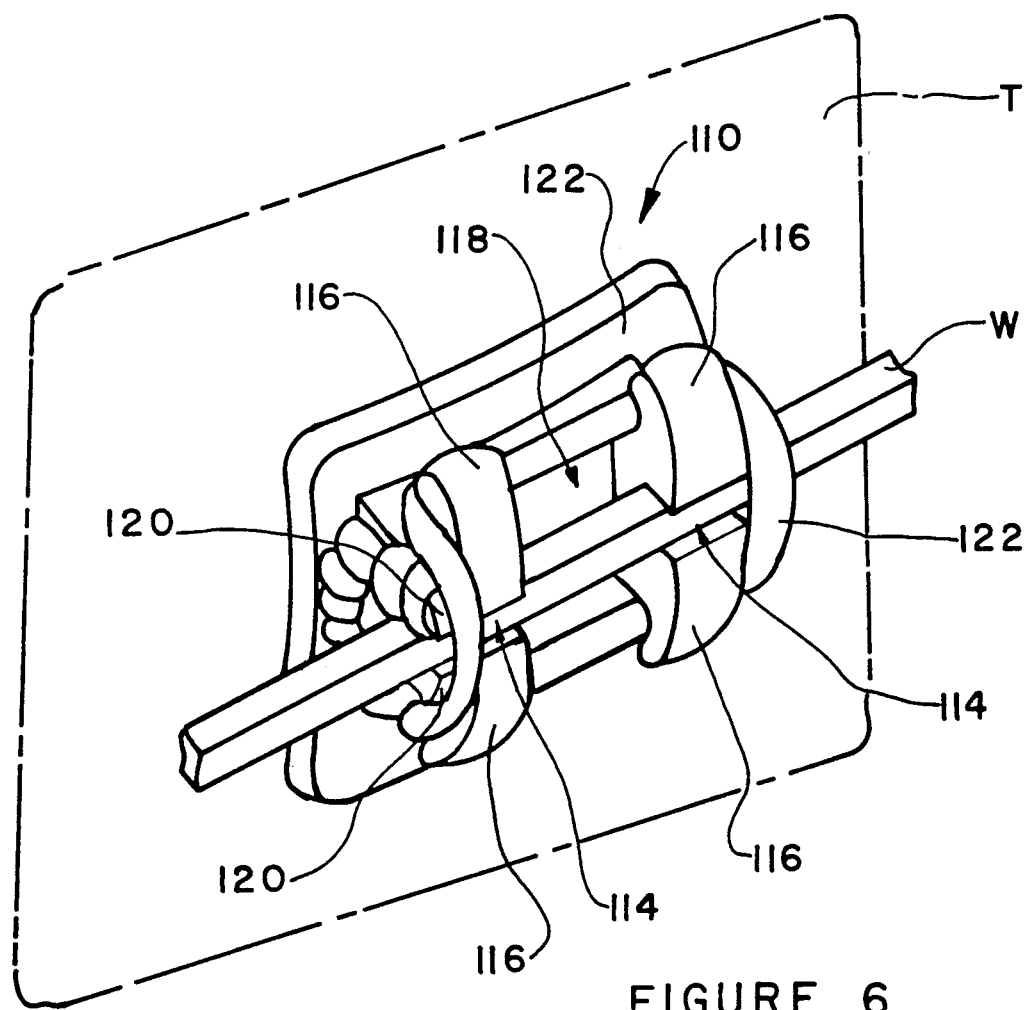
FIG. 6 is another perspective view of the orthodontic appliance of FIG. 5, shown mounted to a tooth with an archwire ligated thereto by a ligature wire.

In FIG. 6, the orthodontic appliance 110 is shown mounted to a tooth T. An archwire W is seated against the bottom surface of the archwire slot 114, and ligated to the orthodontic appliance 110 by a stainless steel ligature wire 122. The ligature wire 122 is wrapped over the distal shoulders 120, under both pairs of tie-wings 116, and up over the mesial shoulders 120. The free ends of the ligature wire 122 are then twisted together beneath the archwire W on the mesial side of the orthodontic appliance 110, as shown in FIG. 6.

As further shown in FIG. 6, when the archwire W is seated against the bottom surface of the archwire slot 114, the top of the archwire W is located below each shoulder 120. Accordingly, when the ligature wire 122 is supported by the shoulders 120, it does not contact the archwire W. As a result, when the tooth T moves during orthodontic treatment, the orthodontic appliance 110 is permitted to move with the tooth T relative to the archwire W.

It should be noted, however, that if necessary for a particular patient, the stainless steel ligature wire 122 can be ligated in contact with the archwire W. The ligature wire 122 would not be supported by the shoulders 120, but would be wrapped in contact with the archwire W on either end of the orthodontic appliance 110. The stainless steel ligature wire 122 would thus be supported directly by the archwire W and maintained in firm contact therewith. Therefore, when using an orthodontic appliance of the present invention, a clinician has the option to permit the appliance to move or not move relative to the archwire during treatment.

Figure 7:
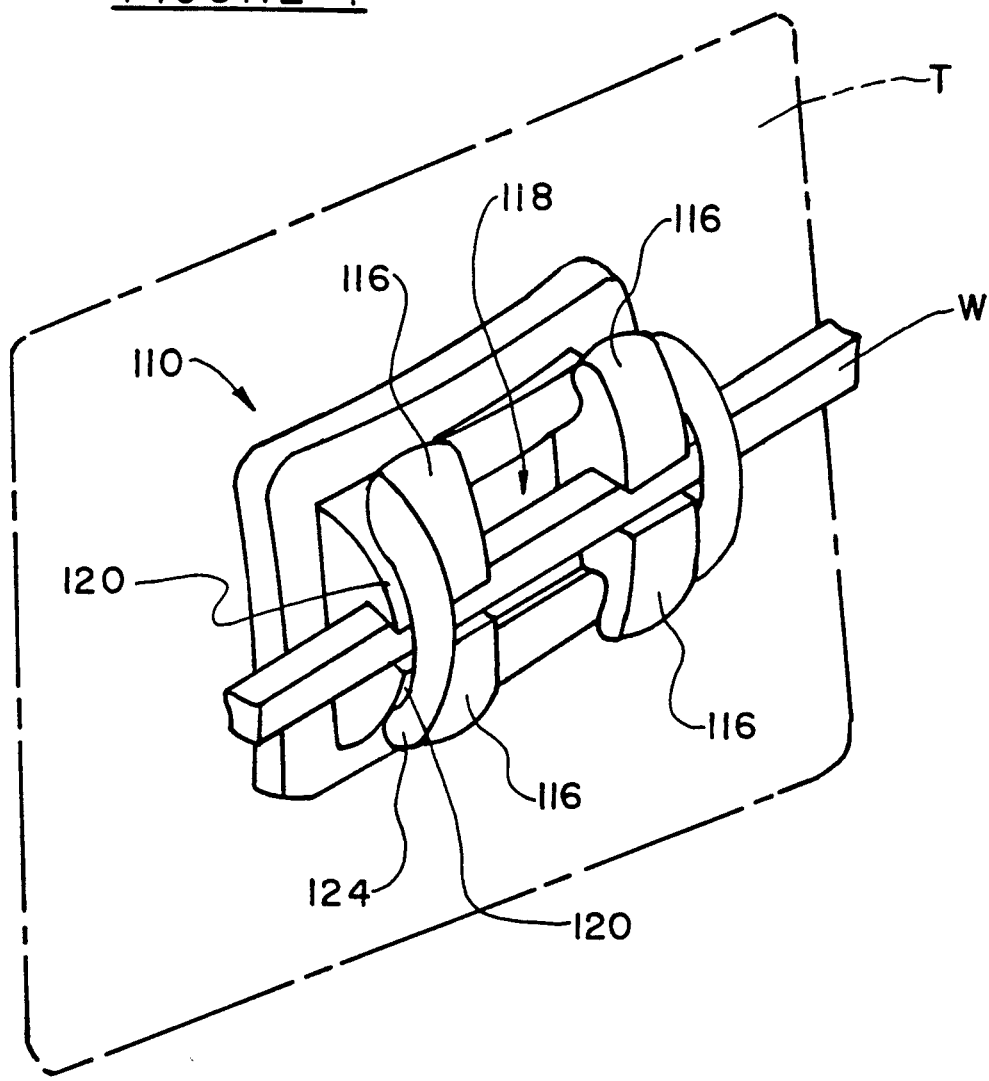
FIG. 7 is another perspective view of the orthodontic appliance of FIG. 5, shown mounted to a tooth with an archwire ligated thereto by an elastic ligature.

In FIG. 7, the orthodontic appliance 110 is shown mounted to a tooth T, with an archwire W ligated thereto by an elastic ligature 124. The elastic ligature 124 is wrapped underneath the tie-wings 116, and over the four shoulders 120. The shoulders 120 support the elastic ligature 124 so that it is spaced above the archwire W, and thus does not contact the archwire. Therefore, like the embodiment described above in relation to FIG. 6, the orthodontic appliance 110 is permitted to move with the tooth T, relative to the archwire W.

It should be noted, however, that like the stainless steel ligature 122, the elastic ligature 124 can be wrapped directly in contact with the archwire W. The elastic ligature 124 would then be wrapped underneath the tie-wings 116 and to the side of each of the four shoulders 120. The elastic ligature would thus be supported by the archwire W and wrapped in firm contact therewith, on either end of the orthodontic appliance 110.

Figure 8:
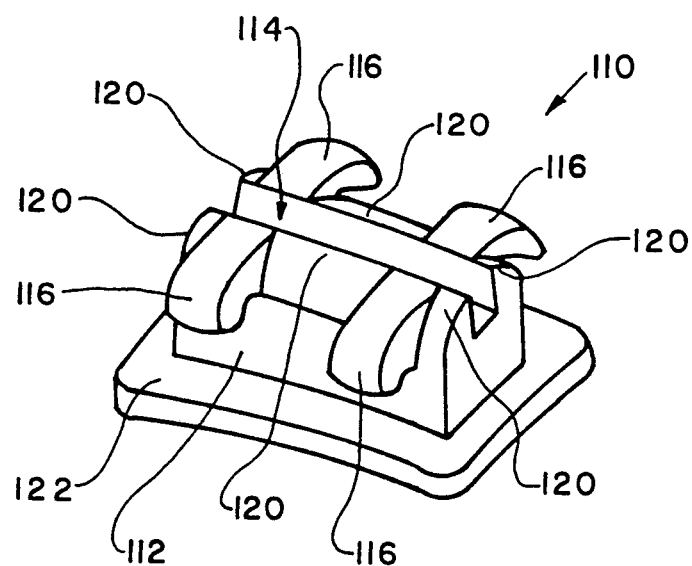
FIG. 8 is a top perspective view of another orthodontic appliance embodying the present invention.

In FIG. 8, another orthodontic appliance embodying the present invention is indicated generally by the reference numeral 110. The orthodontic appliance 110 of FIG. 8 is similar to the orthodontic appliance described above in relation to FIGS. 5 through 7. Therefore, like reference numerals are used to indicate like elements. The orthodontic appliance 110 of FIG. 8 differs from the orthodontic appliance described above, in that the shoulders 120 extend along the length of the archwire slot 114, between the two pairs of tie-wings 116.

The orthodontic appliance 110 of FIG. 8 is particularly suitable for obtaining rotational tooth movement. Either an elastic ligature or a stainless steel ligature wire can be wrapped around only one pair of opposing tie-wings 116, in order to apply a rotationally directed force to the tooth. In such a case, the ligature is supported above the archwire by the shoulders 120 on either side of the respective pair of tie-wings 116. Accordingly, the orthodontic appliance 110 is permitted to move relative to an archwire W with corresponding tooth movement during treatment.

Figure 9:
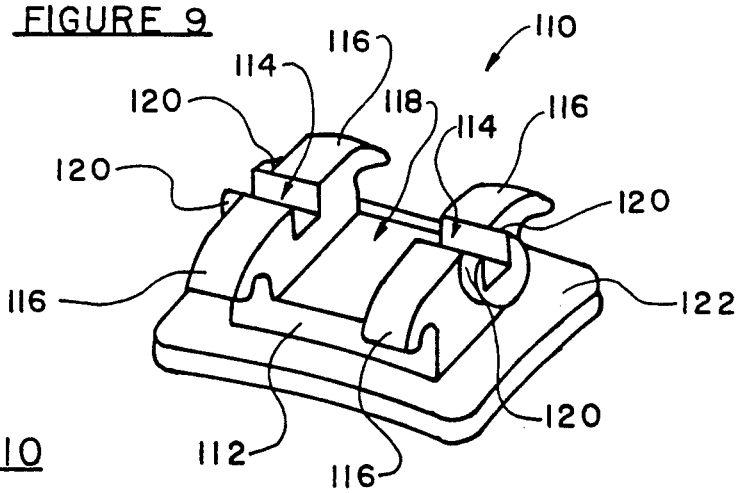
FIG. 9 is a top perspective view of another orthodontic appliance embodying the present invention.

In FIG. 9, another orthodontic appliance embodying the present invention is indicated generally by the reference numeral 110. The orthodontic appliance 110 of FIG. 9 is similar to the orthodontic appliance described above in relation to FIGS. 5 through 7. Therefore, like reference numerals are used to indicate like elements. The orthodontic appliance 110 of FIG. 9 differs from the orthodontic appliance described above, in that the shoulders 120 located on the mesial and distal ends of the orthodontic appliance 110, are each formed by a shoulder member 121.

Each shoulder member 121 projects outwardly from a respective end of the orthodontic appliance 110, each having a respective end of the archwire slot 114 formed therethrough. Each shoulder member 121 defines a radially contoured outer surface, defined substantially by a radius of curvature. Each shoulder 120 is therefore defined by the radially contoured surface and terminates on the top edge of the archwire slot 114. The shoulders 120 are dimensioned so that when the ligature wire is supported thereon, it is spaced above the archwire W by a space S.

Figure 10:
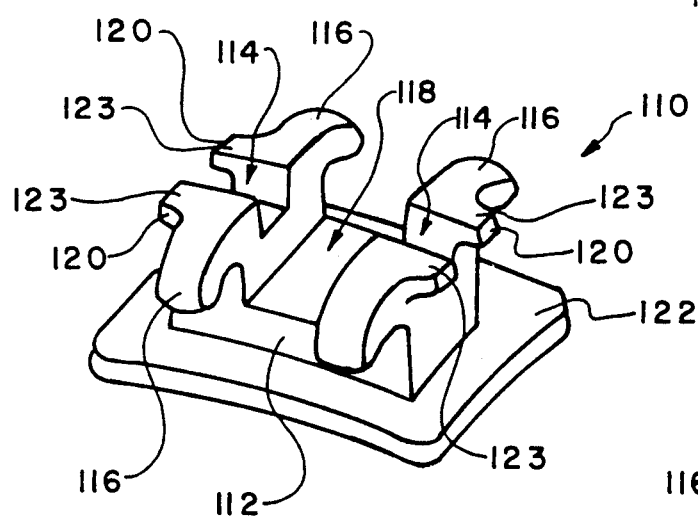
FIG. 10 is a top perspective view of another orthodontic appliance embodying the present invention.

In FIG. 10, another orthodontic appliance embodying the present invention is indicated generally by the reference numeral 110. The orthodontic appliance 110 of FIG. 10 is similar to the orthodontic appliance of FIG. 9 and, therefore, like reference numerals are used to indicate like elements. The orthodontic appliance 110 differs from the orthodontic appliance described above, in that the shoulders 120 each have a substantially different shape than the shoulders described above.

As shown in FIG. 10, two opposing shoulders 120 project outwardly from the tie-wings 116 on opposite sides of the archwire slot 114 in the distal direction. The other two opposing shoulders 120 project outwardly from the other tie-wings 116 on opposite sides of the archwire slot 114, on the other end of the orthodontic appliance. Each shoulder 120 defines a top surface 123 which extends outwardly from the top surface of the adjacent tie-wing 116 in substantially the same plane thereof. The top surfaces 123 are dimensioned relative to the bottom surface of the archwire slot 114, so that when the ligature is supported on the surfaces 123, it is spaced above the archwire W by a space S.

Figure 11:
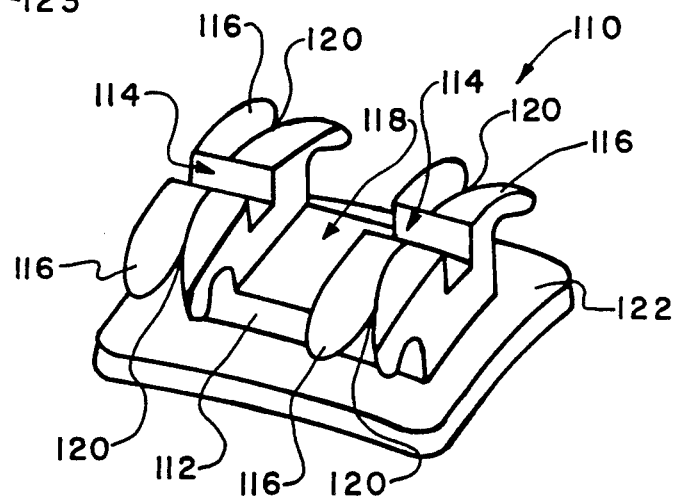
FIG. 11 is a top perspective view of another orthodontic appliance embodying the present invention.

In FIG. 11, another orthodontic appliance embodying the present invention is indicated generally by the reference numeral 110. The orthodontic appliance 110 of FIG. 11 is similar to the orthodontic appliance 110 described above in relation to FIGS. 5 through 7. Therefore, like reference numerals are used to indicate like elements. The orthodontic appliance 110 differs from the orthodontic appliances described above in the construction of the tie-wings 116 and shoulders 120.

As shown in FIG. 11, each tie-wing 116 defines an indentation in the side thereof opposite the archwire slot 114. The surface defining the indentation forms the respective shoulder 120. Each indentation is dimensioned to receive an elastic ligature, or a stainless steel ligature wire therein. Therefore, the ligature (not shown) is wrapped underneath one side of the tie-wing 116 and up through the indentation defining the shoulder 120. The ligature is then wrapped over the shoulder 120 and archwire slot 114, and down through the indentation defined in the opposite tie-wing 116.

The top surface of each tie-wing 116 is dimensioned relative to the bottom surface of the archwire slot 114, so that when an archwire is seated in the archwire slot, a space S is maintained between the top of the archwire and the top surface of the respective tie-wing 116. The ligature is therefore supported by each shoulder 120 above the archwire by the space S.

It should be noted, however, that the ligature can also be wrapped around the end of the orthodontic appliance 110, and not through the shoulders 120, as described above in relation to the other orthodontic appliances. In such a case, the ligature would be wrapped in contact with the archwire and, accordingly, would not permit the archwire to move freely relative to the orthodontic appliance.

I claim:

1. An orthodontic appliance including a bracket portion, comprising:
   an archwire slot defined in the bracket portion, the archwire slot extending substantially in the mesial-distal direction of the appliance and being adapted to receive an archwire therein, the bracket portion including four shoulders on the free ends thereof, two shoulders being located on opposite sides of the archwire slot with respect to each other on the mesial end of the appliance and the other two shoulders being located on opposite sides of the archwire slot with respect to each other on the distal end of the appliance, each shoulder defining a supporting surface, thus forming two supporting surfaces located on either side of the archwire slot on the mesial end of the appliance and two supporting surfaces located on either side of the archwire slot on the distal end of the appliance, each supporting surface supporting a ligature thereon spaced away from an archwire received within the archwire slot to permit the appliance to move relative to the archwire during orthodontic treatment.

2. An orthodontic appliance as defined in claim 1, further comprising:
   at least one pair of tie-wings, each tie-wing projecting outwardly from the bracket portion on an opposite side of the archwire slot with respect to the other tie-wing, the pair of tie-wings being located between the two shoulders on the mesial end of the appliance and the two shoulders on the distal end of the appliance, the tie-wings each being adapted so that ligature can be wrapped underneath each tie-wing and over the shoulders to ligate an archwire to the appliance.

3. An orthodontic appliance as defined in claim 2, wherein
   each supporting surface extends outwardly from the adjacent tie-wing and is located substantially in the same plane as the top surface of the tie-wing.

4. An orthodontic appliance as defined in claim 2, further comprising:
   two pairs of tie-wings spaced apart from each other, one pair of tie-wings being located adjacent to the two shoulders located on the mesial end of the appliance, and the other pair of tie-wings being located adjacent to the two shoulders located on the distal end of the appliance.

5. An orthodontic appliance as defined in claim 1, wherein
   each supporting surface is substantially curved and extends upwardly on the bracket portion and terminates on an edge of the archwire slot.

6. An orthodontic appliance including a bracket portion, comprising:
   an archwire slot defined in the bracket portion, the archwire slot extending substantially in the mesial-distal direction of the appliance and being adapted to receive an archwire therein, the bracket portion including four shoulders on the free end thereof, two shoulders being located on opposite sides of the archwire slot with respect to each other on the mesial end of the appliance and the other two shoulders being located on opposite sides of the archwire slot with respect to each other on the distal end of the appliance, each shoulder being adapted to support a ligature thereon spaced away from an archwire received within the archwire slot to permit the appliance to move relative to the archwire during orthodontic treatment;

two pairs of tie-wings spaced apart from each other, each tie-wing projecting outwardly from the bracket portion on an opposite side of the archwire slot with respect to another tie-wing, one pair of tie-wings being located adjacent to the two shoulders located on the mesial end of the appliance, and the other pair of tie-wings being located adjacent to the two shoulders located on the distal end of the appliance, the tie-wings each being adapted so that ligature can be wrapped underneath each tie-wing and over the shoulders to ligate an archwire to the appliance; and two shoulders located on opposite sides of the archwire slot with respect to each other and extending between the two pairs of tie-wings, each shoulder being adapted to support a ligature thereon so that a space is maintained between the ligature and an archwire received within the archwire slot to permit the appliance to move relative to the archwire during orthodontic treatment.

7. An orthodontic appliance as defined in claim 6, wherein
each shoulder is defined by a substantially curved surface extending upwardly on the bracket portion and terminating on an edge of the archwire slot.

8. An orthodontic appliance including a bracket portion, comprising:
an archwire slot defined in the bracket portion, the archwire slot extending substantially in the mesial-distal direction of the appliance and being adapted to receive an archwire therein, the bracket portion including four shoulders on the free end thereof, two shoulders being located on opposite sides of the archwire slot with respect to each other on the mesial end of the appliance and the other two shoulders being located on opposite sides of the archwire slot with respect to each other on the distal end of the appliance, each shoulder being adapted to support a ligature thereon spaced away from an archwire received within the archwire slot to permit the appliance to move relative to the archwire during orthodontic treatment; wherein
the two shoulders located on the mesial end of the appliance are defined by a first member projecting outwardly from the bracket portion and having one end of the archwire slot formed therethrough; and
the two shoulders located on the distal end of the appliance are defined by a second member projecting outwardly from the bracket portion and having the other end of the archwire slot formed therethrough.

9. An orthodontic appliance as defined in claim 8, wherein
each shoulder is defined by a substantially curved surface of the first or second member, respectively, extending downwardly from the adjacent edge of the archwire slot in substantially the direction of the base member.

10. An orthodontic appliance comprising:
a bracket portion defining an archwire slot extending therethrough, the archwire slot being adapted to receive an archwire therein; and
means for supporting a ligature on the bracket portion including two supporting surfaces located on opposite sides of the archwire slot relative to each other on one end of the appliance and two supporting surfaces located on opposite sides of the archwire slot relative to each other on the other end of the appliance, each supporting surface supporting a ligature spaced away from an archwire received within the archwire slot to permit the appliance to move relative to the archwire during orthodontic treatment.

11. An orthodontic appliance as defined in claim 10, further comprising:
a first pair of tie-wings, each first tie-wing being located on an opposite side of the archwire slot relative to the other and projecting outwardly therefrom, each first tie-wing being located adjacent to a respective first shoulder.

12. An orthodontic appliance as defined in claim 12, further comprising:
a second pair of tie-wings, each second tie-wing being located on an opposite side of the archwire slot relative to the other and projecting outwardly therefrom, the second pair of tie-wings being spaced apart from the first pair of tie-wings, the first and second pairs of tie-wings each being located adjacent to a respective pair of supporting surfaces.

13. An orthodontic appliance as defined in claim 10, wherein
each supporting surface is substantially curved and extends upwardly on the bracket portion and curves inwardly toward the archwire slot and terminates on an edge thereof.

14. An orthodontic appliance comprising:
a bracket portion defining an archwire slot extending therethrough, the archwire slot being adapted to receive an archwire therein;
means for supporting a ligature on the bracket portion for maintaining a space between the ligature and an archwire received within the archwire slot to permit the appliance to move relative to the archwire during orthodontic treatment, wherein the means for supporting includes a first pair of shoulders, each first shoulder being located on an opposite side of the archwire slot relative to the other on the free end of the bracket portion, each first shoulder being adapted to support a ligature thereon so that when an archwire is received within the archwire slot, the ligature is spaced above the archwire;
a first pair of tie-wings, each first tie-wing being located on an opposite side of the archwire slot relative to the other and projecting outwardly therefrom, each first tie-wing being located adjacent to a respective first shoulder, and wherein the means for supporting further includes a second pair of shoulders located on an opposite end of the bracket portion with respect to the first pair of shoulders on the free end thereof, each of the second shoulders being located on an opposite side of the archwire slot relative to the other, the first pair of tie-wings being located between the first and second pairs of shoulders; and a second pair of tie-wings, each second tie-wing being located on an opposite side of the archwire slot relative to the other and projecting outwardly therefrom, the second pair of tie-wings being spaced apart from the first pair of tie-wings, the first and second pairs of tie-wings each being located adjacent to the first and second pairs of shoulders, respectively, and wherein the means for supporting further includes a third pair of shoulders, each third shoulder being located on an opposite side of the archwire slot relative to the other on the free end of the bracket portion, the third pair of shoulders extending between the first and second pairs of tie-wings.

15. An orthodontic appliance comprising:

a bracket portion defining an archwire slot extending therethrough, the archwire slot being adapted to receive an archwire therein;

a pair of tie-wings, each tie-wing projecting outwardly from the bracket portion on an opposite side of the archwire slot relative to the other; and means for supporting a ligature on the bracket portion spaced away from an archwire received within the archwire slot to permit the appliance to move relative to the archwire during orthodontic treatment and including an indentation formed within each respective tie-wing, each indentation being adapted to receive and support a ligature, and to maintain the ligature spaced above an archwire received within the archwire slot.

16. An orthodontic appliance including a bracket portion, comprising:

an archwire slot extending through the bracket portion and being adapted to receive an archwire therein;

a first pair of shoulders located on the free end of the bracket portion, each first shoulder being located on an opposite side of the archwire slot relative to the other and including a support surface for supporting a ligature thereon so that the ligature is spaced above an archwire received within the archwire slot to permit the appliance to move relative to the archwire;

a second pair of shoulders located on the free end of the bracket portion on the other side thereof relative to the first pair, each second shoulder being located on an opposite side of the archwire slot relative to the other and including a support surface for supporting a ligature thereon so that the ligature is spaced above an archwire received within the archwire slot, to permit the appliance to move relative to the archwire; and a first pair of tie-wings located between the first and second pairs of shoulders, each first tie-wing being located on an opposite side of the archwire slot relative to the other, and projecting outwardly therefrom.

17. An orthodontic appliance as defined in claim 16, further comprising:

a second pair of tie-wings spaced apart from the first pair of tie-wings, each second tie-wing being located on an opposite side of the archwire slot relative to the other and projecting outwardly therefrom, the first and second pairs of tie-wings each being located adjacent to the first and second pairs of shoulders, respectively.

* * * * *